United States Patent [19]

Biola et al.

[11] 4,225,516
[45] Sep. 30, 1980

[54] PROCESS FOR THE MANUFACTURE OF BETA-METHYLTHIOPROPIONALDEHYDE

[75] Inventors: Georges Biola, Venissieux; Yves Komorn, Lyons; Eric Limongi, Villeurbanne, all of France

[73] Assignee: Rhone-Poulenc Industries, Paris, France

[21] Appl. No.: 696,432

[22] Filed: Jun. 15, 1976

[30] Foreign Application Priority Data

Jun. 20, 1975 [FR] France .................. 75 20183

[51] Int. Cl.³ .................... C07C 47/02; C07C 151/00
[52] U.S. Cl. .................................................. 568/41

[58] Field of Search .......... 260/601 R, 609 B, 615 A, 260/601

[56] References Cited

U.S. PATENT DOCUMENTS

| 3,529,940 | 9/1970 | Shima et al. | 260/601 R |
| 3,574,766 | 4/1971 | Meyer et al. | 260/601 R |

*Primary Examiner*—Werren B. Lone
*Attorney, Agent, or Firm*—Burns, Doane, Swecker & Mathis

[57] ABSTRACT

Beta-methylthiopropionaldehyde is prepared from methylmercaptan and an acrolein-containing gaseous mixture derived as an off-gas from the catalytic oxidation of propylene.

16 Claims, 1 Drawing Figure

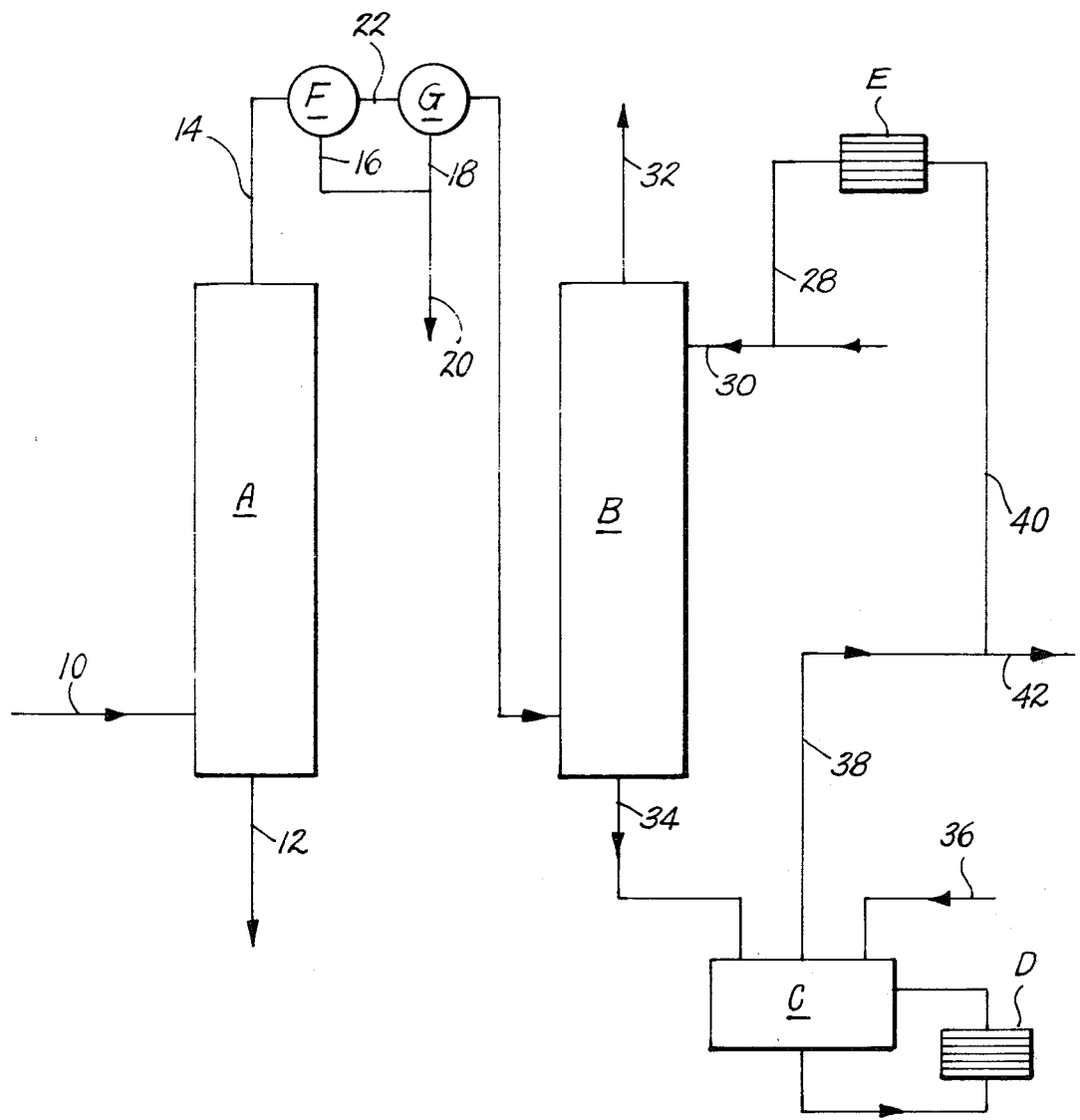

PROCESS FOR THE MANUFACTURE OF BETA-METHYLTHIOPROPIONALDEHYDE

BACKGROUND OF THE INVENTION

1. Field of the Invention

The present invention relates to an improvement in the process for the manufacture of beta-methylthiopropionaldehyde (hereinafter referred to as MTPA) from methylmercaptan and an acrolein containing off-gass originating from the catalytic oxidation of propylene.

2. Description of the Prior Art

It is known to prepare MTPA from methylmercaptan and a gas mixture containing acrolein, which has been obtained by catalytic oxidation of propylene. For example, Netherlands Patent Application No. 68/09,647 describes a process whereby MTPA is obtained in the liquid state in a reaction zone, by absorption of a gas mixture containing acrolein, by the MTPA, and reaction of the acrolein dissolved in the MTPA with methylmercaptan. According to this process, it is also possible to first bring the methylmercaptan into contact with the MTPA in a reaction zone, and then contact the mixture thus obtained with a gas containing the acrolein. In these two variants, the formation of the MTPA is conducted in the presence of an aqueous solution at a pH of between 4 and 7, and the MTPA is recirculated into the reaction zone. However, it is thus necessary to carry out a supplementary stage of an extraction treatment of the aqueous phase of the liquid product obtained to obtain a total yield of MTPA of about 91%. On a commercial scale, the mandatory extraction step in this and other similar processes obviously increases the cost of production while complicating the overall method. Accordingly, the need exists to simply, yet highly efficiently and economically, produce MTPA from methylmercaptan and an acrolein-containing gas.

SUMMARY OF THE INVENTION

In accordance with the noted, and notable, deficiencies of the prior art, it is a primary object of the present invention to produce MTPA in a simple, yet highly efficient and economical manner which eliminates the necessity for an extraction step to remove aqueous components.

It is also a primary object of the present invention to produce MTPA by reacting an acrolein-containing gas borne in a suitable carrier with methylmercaptan, which process eliminates the requisite extraction step of prior art processes.

It is yet another object of the present invention to produce commercial quantities of MTPA through a process which provides yields approaching 100%.

Still a further object of the present invention is to produce MTPA in a process which recycles a portion of the MTPA to a reaction zone for use as an ideal carrier for an acrolein-containing gas which is reacted with methylmercaptan to yield MTPA.

Yet further objects and advantages of the present invention will become apparent to the skilled artisan upon examination of the detailed description of the invention.

In accordance with the foregoing objects and advantages of the present invention, it has surprisingly been determined that MTPA may be prepared from the acrolein contained in an off-gas originating from the catalytic oxidation of propylene in an anhydrous medium. Furthermore, it has been determined that the process according to the present invention provides yields of MTPA close to 100%. According to the process of the present invention, essentially two steps are required, the first of which consists of absorption of a gas mixture containing acrolein by MTPA, and the second of which is the reaction between acrolein dissolved in the MTPA and methylmercaptan at a temperature of between 10 and 50° C. The process is characterized in that prior to the absorption, the gas mixture is freed from the acrylic acid and water which it contains, and the content of hemithioacetal formed in the reaction mixture is regulated between 0 and 1% by weight.

BRIEF DESCRIPTION OF THE DRAWINGS

The sole FIGURE of drawing is a diagrammatic representation of an apparatus useful for practicing the process of the present invention.

DETAILED DESCRIPTION OF THE INVENTION

The present invention relates broadly to a process for the manufacture of MTPA from methylmercaptan and an acrolein-containing gas. The acrolein is preferably obtained from the catalytic oxidation of propylene as an off-gas from that process, and is abosrbed by an MTPA carrier for subsequent reaction with the methylmercaptan.

In order to more fully elucidate upon the various objects and advantages of the present invention, preferred embodiments thereof will be given, the same intended to be illustrative and in no wise limitative.

The process of the present invention comprises essentially two steps:

(1) an acrolein-containing off-gas resulting from the catalytic oxidation of propylene is absorbed or dissolved in an MTPA carrier; and, (2) this mixture is reacted in a reaction zone with methylmercaptan.

Preferably, the reaction between the acrolein dissolved in the MTPA and the methylmercaptan is conducted at a temperature within the range of from about 10 to about 50° C., during which reaction is hemithioacetal of MTPA is formed, preferably within the range of from about 0 to about 1% by weight.

The acrolein-containing gas employed in the present invention results from the catalytic oxidation of propylene in any conventional manner. Regardless of the oxidation process employed, the off-gas resulting therefrom typically contains oxygen, nitrogen, carbon monoxide, carbon dioxide, water, acrylic acid, acrolein, acetaldehyde, and various other compounds. This off-gas is pre-treated prior to the absorption by the MTPA, to remove the water and acrylic acid content. The acrylic acid component, typically present in molar proportions of from about 0.2 to about 2.0% is removed in any conventional manner. For example, the acrylic acid may be absorbed in water or in such solvents and tributyl phosphate or a mixture of diphenyl ether and diphenyl. Once the acrylic acid constituent has been removed, the water component is expressed by passing the off-gas through a condensor having, preferably, a final condensation temperature between 0° and −5° C.

The significance of these preliminary treatments resides in the minimization of degradative reactions of the MTPA produced during the reaction between the acrolein dissolved therein and the methylmercaptan. Particularly, it has been determined that the presence of water in this reaction mixture leads to the formation of objectional residues detrimental to the ultimate yield of the reaction. Thus, it is essential that the reactants be anhydrous.

Following the condensation of the off-gas, the gas is directed to an absorption column in which the MTPA circulates in counter-current fashion. The MTPA may be provided to this absorption column either from an independent source (either pure or technical grade) or, more preferably, as a crude recycle MTPA produced during the subsequent reaction.

Regardless of the source of MTPA, the absorption of the acrolein-containing gas is conducted at temperatures of about 40° C., or less. Therefore, the temperature of the MTPA feed stream to the column is advantageously maintained within a range from about 0° to about $-15°$ C. and, most preferably, at about $-10°$ C., which results in an absorption temperature, at the bottom of the column, of between about 0° and about 40° C., most preferably about 25° C. Depending upon the temperature conditions within the absorption column, as well as the feed rate of the incoming stream of MTPA, the concentration of acrolein in the MTPA leaving the column will vary; however, under the preferred conditions it has been found to vary between about 5 and about 20% by weight.

The acrolein absorbed by the MTPA is thence directed to a reactor wherein it is reacted with methylmercaptan in the presence of a suitable catalyst. The operative reactions whereby MTPA is synthesized are as follows:

(1) Addition reaction of methylmercaptan with MTPA, yielding the hemithioacetal of MTPA, in accordance with the equation:

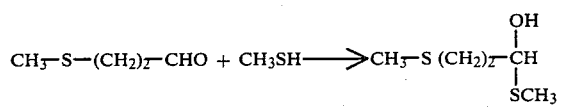

(2) Reaction of acrolein with hemithioacetal, in accordance with the equation:

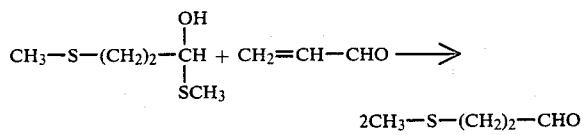

Thus, the overall reaction may be described by the following equation:

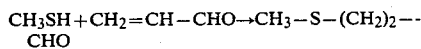

Among the catalysts found suitable for the reaction of the acrolein absorbed by the MTPA with methylmercaptan are triethylamine, hexamethylenetetramine, pyridine and other typical organic bases, as well as mixtures of organic acids and organic bases such as a mixture of acetic acid and pyridine or acetic acid and triethylamine. Other possible catalysts may include neutral amino acid, mecury methylmercaptide, organic peroxides, cupric acetate, ion exchange resins, and the like.

The temperature of reaction desirably is within the range of from about 10° to about 50° C., and preferably at about 30° C. It has been determined that at reaction temperatures greater than 50° C. the selectivity with respect to formation of MTPA is significantly decreased. Likewise, it has been learned that reaction temperatures below about 10° C. provide slow reaction kinetics and, thus, requires a greater technological capital investment.

Reaction pressure has not been found to be a critical factor in conducting the reaction and may vary within broad limits. However, it is preferred that the reaction according to the present invention be conducted at about atmospheric pressure.

Similarly, reaction time may vary within a broad range. Under conditions typically obtaining in industrial environments, the reaction time varies between about 0.5 and about 1.0 hours.

According to one aspect of the present invention, the hemithioacetal content of the MTPA in the reaction mixture is adjusted to be greater than 0 but less than 1% by weight, and preferably between 0.1 and 0.2%. Too little hemithioacetal content has been found to result in a loss of acrolein due to incomplete reaction. Should the hemithioacetal content be greater than 1%, however, substantial degradation of the MTPA occurs in the reaction zone, a condition obviously detrimental to optimum yields of the present process, which approach 100% when the preferred embodiment is employed.

The hemithioacetal content of the MTPA may be maintained within the critical limits of the invention by suitably adjusting reaction parameters and, particularly, by appropriate regulation of the respective flow rates of the liquid methylmercaptan and the MTPA-acrolein solution obtained from the absorption column, which feed streams are brought into contact within a reaction vessel. The maintenance of a slight excess of hemithioacetal in the mixture, in order to achieve optimum reaction with correspondingly less degradation, corresponds to the regulation of the flow rates of the reaction products whereby a slight excess of methylmercaptan in the reaction mixture is maintained.

It is envisioned within the scope of the invention to react the reaction components with a slight excess of acrolein present; however, the consumption of reactants in such a case has been found to deviate from that considered optimum and, moreover, customary analytical techniques do not permit the same ease of control of the reaction as is possible otherwise. This, in fact, is an additional advantage of maintaining the hemithioacetal content of the MTPA within the broad range of from 0 to 1%, as this results in a significantly improved ability to control the development of the reaction. The determination of hemithioacetal content in the reaction mixture may be made by any appropriate means and, particularly, by extracting samples and conducting an automatic determination of hemithioacetal content by known methods. According to a preferred embodiment of the present invention, the hemithioacetal content of the MTPA is potentiometrically determined.

A portion of the MTPA obtained in accordance with the process of the present invention is recycled to the absorption column wherein the pre-treated acrolein-containing off-gas is contacted. The remaining portion is withdrawn, purified by distillation and stored for subsequent usage. Under the preferred conditions outlined above, the amount recycled to the absorption column corresponds to from about 2 to about 10 times, and preferably 5 times, the amount of MTPA ultimately purified and stored. However, the precise amount of MTPA recycled is not crucial to the realization of the objects and advantages of the present invention and, accordingly, may vary widely within those limits determined optimum for industrial operation.

The process of the present invention is exemplified below, with reference to the FIGURE of drawing; however, this is intended to be illustrative and not limitative of the scope of the invention.

EXAMPLE

The apparatus diagrammatically illustrated in the FIGURE of drawing is comprised of plural absorption columns A and B and a reaction vessel C. Heat exchangers D and E are provided to appropriately control the temperature of feed streams to the reaction vessel C and absorption column B, respectively. Plural condensors F and G are provided: condensor F is water-cooled, while condensor G is brine-cooled.

An off-gas from the synthesis reaction of acrolein is introduced to the bottom of absorption column A through line 10. The typical composition of such an off-gas, in mol percent, is:

$O_2$: 3.1
$N_2$: 41.6
Propylene: 0.33
Water: 48.2
Acrylic acid: 0.65
Acrolein: 5.55
Acetaldehyde: 0.15
Miscellaneous: 0.45 Acrylic acid is separated from the acrolein-containing gas and delivered from absorption column A via line 12.

The off-gas, after having the acrylic acid component removed therefrom, is directed to a first condensor F via line 14. Condensor F is cooled with water having a condensor outlet temperature of about 30° C. Water removed from the off-gas in condensor F is routed through line 16. Subsequently, the off-gas is directed to a condensor G which is brine-cooled and has a condensor outlet temperature of from about 0° C. to about −5° C. Any water remaining after treatment in condensor F is thus removed in condensor G and routed via line 18. Water thus collected in lines 16, 18 is removed via line 20. A small amount of acrolein, on the order of about 10% of the initial amount contained in the off-gas, is also condensed within condensors F and G and removed with the water component via line 20.

The non-condensed gases from condensor G are directed to a second absorption column B via line 24 and enter at the bottom thereof. MTPA may be fed from an external source via line 26, or may be recycled and directed via line 28 to an inlet, 30, at the top of absorption column B. Thus, within absorption column B there is counter-current flow of acrolein-containing off-gas and liquid MTPA. The MTPA injected at the top of absorption column B enters at about −10° C. Should the source be separate from that subsequently produced in the present process, it may be either a pure or technical-grade MTPA. However, the crude MTPA produced and recycled is preferred for matters of expediency and economy. Regardless, however, of the source of the MTPA injected, the absorption temperature obtaining, whereby the acrolein gas is absorbed within the MTPA, is about 25° C.

The gases freed from the acrolein now absorbed within the MTPA are passed through line 32 to a post-combustion section, (not shown). At the bottom of column B a solution of about 10% acrolein dissolved in the MTPA is recovered and passed to reactor C via line 34.

The reactor C is maintained at about atmospheric pressure under a nitrogen atmosphere. Methylmercaptan is simultaneously injected to reactor C via line 36 wherein the respective feed streams react in accordance with the equations given above. The reactor C also has a feed of catalyst, preferably acetic acid/triethylamine which comprises approximately 0.1% of the reaction mixture. Optionally, the acrolein fraction separated from the condensates during the dehydrating of the off-gas may also be fed to the reactor C.

Reaction C is maintained at a temperature of about 30° C. by means of heat exchanger D located in an external recirculation loop which also serves to homogenize the reaction mixture.

The hemithioacetal content of the MTPA is regulated at about 0.15% by appropriately adjusting the various feed rates of reactants to reactor C and periodically sampling and analyzing the reaction mixture for hemithioacetal. Preferably, the analysis is conducted potentiometrically.

Crude MTPA produced in reactor C is withdrawn through line 38. Optionally, and preferably, a portion of the crude MTPA is split from the main stream and recycled via line 40 to absorption column B. The remaining portion of the MTPA is routed via line 42 to separate purification apparatus (not shown) and is then stored. The amount of MTPA recycled preferably is about five times that delivered for purification and storage.

The portion of the MTPA recycled via line 40 is first cooled in heat exchanger E before injection into absorption column B. Preferably, this incoming feed stream is cooled to about −10° C.

Table 1 sets forth the materials' balance for the preferred embodiment described above, wherein the flow rates indicated are in terms of kg/hr.

| Line No.<br>Products | 24 | 30 | 32 | 34 | 36 | 42 |
|---|---|---|---|---|---|---|
| Non-condensable mater | 14.377 | | 14.377 | | | |
| $H_2O$ | 0.041 | 0.231 | 0.002 | 0.270 | | 0.039 |
| Acrolein | 2.347 | | 0.001 | 2.346 | | |
| Acetaldehyde | 0.058 | 0.219 | 0.021 | 0.256 | | 0.037 |
| Methylmercaptan | | | | | 2.015 | |
| Hemithioacetal | | 0.053 | | 0.053 | | 0.009 |
| MTPA | | 25.800 | 0.011 | 25.789 | | 4.352 |

The total yield of MTPA obtained, relative to the acrolein introduced into absorption column B, was 99%.

While the present invention has now been described in terms of preferred embodiments, and exemplified in terms of a preferred embodiment, the skilled artisan will appreciate that various changes, modifications, substitutions, and omissions may be made without departing from the spirit thereof. Accordingly, it is intended that the scope of the invention be limited solely by that of the following claims.

What is claimed is:

1. A method for producing beta-methylthiopropionaldehyde from methylmercaptan and an acrolein-containing gas comprising the steps of:
   (a) absorbing acrolein in a feedstream of betamethylthiopropionaldehyde; and,
   (b) reacting the mixture (a) with methylmercaptan in the substantial absence of water at a temperature within the range of from about 10° C. to about 50°

C., wherein the reaction is accompanied by the formation of hemithioacetal as an intermediate.

2. The method of claim 1, wherein the formation of hemithioacetal is maintained within the range of from greater than 0% to about 1% of the reaction mixture.

3. The method of claim 2, wherein said hemithioacetal is maintained between 0.1% and 0.2%.

4. The method of claim 3, wherein the regulation of said hemithioacetal is achieved by controlling the feed rates of reactants to the reaction vessel therefor.

5. The method of claim 1, wherein said acrolein is obtained as the off-gas from the catalytic oxidation of propylene, said method further including the steps of:
   (a) removing substantially all of the acrylic acid component of said off-gas; and,
   (b) condensing essentially all of the water component of said off-gas to substantially, completely remove said water component from said off-gas.

6. The method of claim 5, wherein said absorbing step comprises:
   (a) feeding an anhydrous stream of the acrolein-gontaining gas to an absorption column, said gas being maintained at a temperature within the range of from about 0° C. to about −5° C.; and,
   (b) feeding a stream of liquid beta-methylthiopropionaldehyde to said absorption column, said stream of liquid being maintained at a temperature within the range of from about 0° C. to about −15° C.

7. The method of claim 6, wherein said feedstreams contact each other in counter-current relationship.

8. The method of claim 6, wherein said reacting step includes reacting said mixture of acrolein and betamethylthiopropionaldehyde with said methylmercaptan in the presence of a catalyst.

9. The method of claim 8, wherein said catalyst is an acetic acid/triethylamine mixture and is present as 0.1% of the reaction mixture.

10. The method of claim 7, wherein the product of said reacting step is divided into two streams, a first of which is recycled to said absorbing step.

11. The method of claim 10, wherein said first stream is from about 2 to about 10 times the volume of the second.

12. The method of claim 11, wherein said first stream if 5 times the volume of the second.

13. The method of claim 6, wherein said absorbing step is conducted at a temperature within the range of from about 0° C. to about 40° C.

14. The method of claim 13, wherein said beta-methylthiopropionaldehyde feedstream to said absorption column is maintained at a temperature of about −10° C., and wherein said absorbing step is conducted at a temperature about 25° C.

15. The method of claim 13, wherein said reacting step is conducted at a temperature of from about 10° C. to about 50° C.

16. The method of claim 13, wherein said reacting step is conducted at a temperature of about 30° C.

* * * * *